(12) United States Patent
Chiu et al.

(10) Patent No.: US 8,840,810 B2
(45) Date of Patent: Sep. 23, 2014

(54) BENZOFURANONE DERIVATIVES AND APPLICATION OF THE SAME

(75) Inventors: Ching-Fan Chiu, Taipei (TW); Ching-Yie Su, New Taipei (TW); Eric Lee, Taipei (TW)

(73) Assignees: Chitec Technology Co., Ltd., Taipei (TW); Double Bond Chemical Ind., Co., Ltd., New Taipei (TW); FDC, Lees Chemical Industry Co. Ltd., Taipei (TW)

( * ) Notice: Subject to any disclaimer, the term of this patent is extended or adjusted under 35 U.S.C. 154(b) by 575 days.

(21) Appl. No.: 13/137,530

(22) Filed: Aug. 24, 2011

(65) Prior Publication Data

US 2012/0238677 A1   Sep. 20, 2012

(30) Foreign Application Priority Data

Mar. 17, 2011   (TW) .............................. 100109042 A (51) Int. Cl.
| | | |
|---|---|---|
| *C09K 15/08* | (2006.01) | |
| *C09K 15/06* | (2006.01) | |
| *C07D 307/79* | (2006.01) | |
| *C07D 307/83* | (2006.01) | |
| *C08K 5/1535* | (2006.01) | |

(52) U.S. Cl.
CPC ............ *C07D 307/83* (2013.01); *C08K 5/1535* (2013.01)
USPC ............ 252/407; 252/404; 549/466; 524/111

(58) Field of Classification Search
USPC ................... 252/404, 407; 524/111; 549/466
See application file for complete search history.

(56) References Cited

U.S. PATENT DOCUMENTS

| | | | |
|---|---|---|---|
| 4,325,863 | A | 4/1982 | Hinsken et al. |
| 4,338,244 | A | 7/1982 | Hinsken et al. |
| 5,607,624 | A | 3/1997 | Nesvadba et al. |
| 2003/0109611 | A1 | 6/2003 | Schrinner et al. |

FOREIGN PATENT DOCUMENTS

JP     2009057453 A  *  3/2009

OTHER PUBLICATIONS

English machine translation of Iwamoto et al., JP 2009057453A (Mar. 2009).*
Frenette et al., "Radically Different Antioxidants: Thermally Generated Carbon-Centered Radicals as Chain-Breaking Antioxidants", J. Am. Chem. Soc., 2006, vol. 128, pp. 16,432-16,433.

* cited by examiner

*Primary Examiner* — Peter F Godenschwager
(74) *Attorney, Agent, or Firm* — Bacon & Thomas, PLLC (57) ABSTRACT

The present invention relates to the antioxidant compounds which are synthesized or derived from benzofuranone compound and benzoic acid compound. The antioxidant compound with remarkable heat resistance possesses carbon-centered radical quencher and primary antioxidant synergism. It can be use as additive for polymer to enhance its stability of melting flow and color.

12 Claims, 12 Drawing Sheets

BENZOFURANONE DERIVATIVES AND APPLICATION OF THE SAME

BACKGROUND OF THE INVENTION

1. Field of Invention

The present invention relates to benzofuranone derivatives. Furthermore, the present invention relates to benzofuranone derivatives used to add into plastic for improving the antioxidant ability of the polymer.

2. Background Art

When plastic is produced and processed, high temperature thermal treatment is required. During the process, the generation of free radicals and peroxides causes the fast deterioration of the plastic and reduces its physical and mechanical properties. To maintain the physical properties of the plastic, additives such as antioxidant which can capture and quench the free radicals and peroxides are widely used for plastic processing.

Antioxidants can be categorized into 3 types according to their distinct mechanisms. The first type works by capturing and quenching carbon-centered radicals, and it is called "carbon-centered radical antioxidant". The second type has a structure of hindered phenol which works by capturing and quenching the carbon peroxides or the free radicals of oxides, and it is called "primary antioxidant". The representative of the third type is phosphate which works by capturing and quenching the peroxides, and it is called "secondary antioxidant". Since carbon-centered radicals are generated at the first stage during the oxidation of plastic, quenching the radical immediately will be the most effective way to protect the desired materials.

There are a few types of carbon-centered radical antioxidants; one of them is the compound with benzofuranone structure as shown below (formula (A)). Antioxidants with this kind of structure were first developed by Sandoz in 1980s (U.S. Pat. No. 4,325,863, U.S. Pat. No. 4,338,244).

(A)

But only till the middle of 1990s did Ciba introduce the first commodity with benzofuranone structure, Irganox HP-136 (as shown below, formula (B)). This antioxidant delivers excellent effects when it combines with the primary and secondary antioxidants, especially for polyolefin plastics. But it is not thermal stable due to its small molecule.

(B)

Unfortunately, the intermediate (as shown below, formula (C)) of the process for producing HP-136 raised health concerns. The commodity was discontinued from the market afterwards.

(C)

A new antioxidant with benzofuranone structure as shown in the following formula (D) was disclosed in US 2003/0109611. However, the use of this antioxidant is limited to engineering plastics such as PBT and PU. There is no application data for polyolefin plastics.

(D)

The mechanism of benzofuranone antioxidants was first published by J. Am. Chem. Soc., 2006, vol. 128, pp 16,432-16,433. The experiment demonstrated that the active hydrogen of the furan can transfer to the sterically uncrowded position of the carbonyl group by resonance, thus such kind of molecule can quench carbon-centered radicals effectively.

The hindered phenolic primary antioxidant is currently the largest single family of antioxidants, and many derivatives are included. Among these derivatives, those with COOH group are the most popular primary antioxidants to be applied for synthesizing large molecules. Below are some examples of hindered phenolic primary antioxidants.

The combination of the primary antioxidant of hindered phenol series and a variety of secondary antioxidants has been reported and commercialized (as the formula shown below). Adding the single molecule which functionally combines the primary and secondary antioxidants outperforms adding the primary or the secondary antioxidant individually. However, no publication has revealed that carbon-centered radical antioxidant and primary antioxidant can be combined in one molecule.

According to the disclosure of prior art, the derivatives of benzofuranone may provide an excellent antioxidation ability to become a good thermal stability protector. If the benzofuranone derivatives can be functionally combined with a primary antioxidant to provide a synergistic effect in antioxidation, it will be a highly desired product in the plastic field.

SUMMARY OF THE INVENTION

The present invention attempts to develop an antioxidant with the properties of both carbon-centered radical antioxidant and primary antioxidant. When it is added into plastic, the flowability and color stability of the plastic are improved.

To achieve this objective, the present invention presents a benzofuranone derivative with antioxidant ability, which is provided with formula (I) as follow:

wherein n=0, 1, 2, or 3; $R_1$ and $R_2$ independently represent H or C1-C8 alkyl group; $R_3$ and $R_4$ independently represent H or C1-C6 alkyl group and excluding C1-C6 alkyl group simultaneously; $R_5$ and $R_6$ independently represent H or C1-C6 alkyl group and excluding C1-C6 alkyl group simultaneously; and $R_7$ is H or OH.

Furthermore, the present invention provides a method for stabilizing organic materials. The steps of this method include adding a compound with the following formula (I) structure:

wherein n=0, 1, 2, or 3; $R_1$ and $R_2$ independently represent H or C1-C8 alkyl group; $R_3$ and $R_4$ independently represent H or C1-C6 alkyl group and excluding C1-C6 alkyl group simultaneously; $R_5$ and $R_6$ independently represent H or C1-C6 alkyl group and excluding C1-C6 alkyl group simultaneously; and $R_7$ is H or OH.

The antioxidant of the present invention is used as an additive for organic materials. The plastic added with the antioxidant is provided with better flowability and heat resistance. Furthermore, it causes less discoloration under high temperature. The present invention is especially suitable for adding into polymer materials to improve material stability.

DETAILED DESCRIPTION OF THE PRESENT INVENTION

The benzofuranone derivative with antioxidation ability of the present invention is provided with formula (I) as follow:

wherein n=0, 1, 2, or 3; $R_1$ and $R_2$ independently represent H or C1-C8 alkyl group; $R_3$ and $R_4$ independently represent H or C1-C6 alkyl group and excluding C1-C6 alkyl group simultaneously; $R_5$ and $R_6$ independently represent H or C1-C6 alkyl group and excluding C1-C6 alkyl group simultaneously; and $R_7$ is H or OH.

In one preferable embodiment, the $R_3$ is H, and $R_4$ is C3-C5 alkyl group.

In one preferable embodiment, the $R_5$ is H, and $R_6$ is C3-C5 alkyl group.

In a more preferable embodiment, the benzofuranone derivative is provided with formula (II), (III) or (IV) as follow:

(II)

(III)

(IV)

According to the rule for naming, compound (II) could be named as [4-tert-butyl-2-(5-tert-butyl-2-oxo-3H-benzofuran-3-yl)phenyl]benzoate (It is also called for short as compound (II) or CT-500). Compound (III) could be named as [4-tert-butyl-2-(5-tert-butyl-2-oxo-3H-benzofuran-3-yl)phenyl]-3,5-di(tert-butyl)-4-hydroxy-benzoate (It is also called for short as compound (III) or CT-501). Compound (IV) could be named as [4-tert-butyl-2-(5-tert-butyl-2-oxo-3H-benzofuran-3-yl)phenyl]-3-[3,5-di(tert-butyl)-4-hydroxyphenyl]-propanoate (It is also called for short as compound (IV) or CT-502).

The present invention also provides a method for stabilizing organic materials. The procedure includes adding a compound with the following formula (I) structure into aforesaid materials:

(I)

wherein n=0, 1, 2, or 3; $R_1$ and $R_2$ independently represent H or C1-C8 alkyl group; $R_3$ and $R_4$ independently represent H or C1-C6 alkyl group and excluding C1-C6 alkyl group simultaneously; $R_5$ and $R_6$ independently represent H or C1-C6 alkyl group and excluding C1-C6 alkyl group simultaneously; and $R_7$ is H or OH.

In one preferable embodiment, the $R_3$ is H, and $R_4$ is C3-C5 alkyl group.

In one preferable embodiment, the $R_5$ is H, and $R_6$ is C3-C5 alkyl group.

The compound with formula (I) used for stabilizing organic materials in the present invention could be classified as an antioxidant. When adding into the organic materials, the quantity of the compound (I) relative to the organic materials is 0.01%~10% by weight.

In one preferable embodiment, the quantity of the compound (I) relative to the organic materials is 0.1%~2% by weight.

In a more preferable embodiment, the compound (I) is provided with formula (II), (III) or (IV) as follow:

(II)

(III)

-continued (IV)

The compound of the present invention could be added into organic materials, especially polymer materials, to improve their thermal stability, and to prevent oxidation or decomposition. It also provides a better flowability for processing the materials. The suitable polymer materials include, but not limit to polyolefin, olefin copolymer, polystyrene, polyparamethylstyrene, polymethylstyrene or the copolymer or the branched copolymer of the same, polymer or copolymer with halogen, homopolymer or copolymer of cyclic ethers, polyaldehyde, polyphenylene oxide, polyphenylene sulfide, polycyanurethane, polyamide and amide copolymer, polyurea, polyimide, polyamide-imide, polycarbonate, polyester/carbonate, unsaturated polyester resin, thermalsetting acrylate resin or acrylate resin containing melamine resin, urea resin or polycyanate or epoxy resin of the mixture of aforesaid various polymer.

Furthermore, the present invention could be used with any given auxiliary for organic materials. The auxiliary may include antioxidant, UV absorber and light stabilizer, metal deactivator, phosphate ester and phosphite ester, base-costabilizer, nucleating agent, filler and intensifier, plasticizer, lubricant, emulsifier, surfactant, coloring matter, optical brightener, flame retardant, antistatic additive and blowing agent, especially antioxidant. It could be combined with the traditional phosphorous-based antioxidant or the hindered phenol-based antioxidant to let the organic materials with these additives equipped with a superior thermal resistance, antioxidation ability and a better flowability for processing.

It should be easily understood that the compound of the present invention and the use and application of the same are not limited by the different synthesis ways for producing the compound. The exemplified examples of synthesis are used to prove the existence of the compound of the present invention, not to limit the scope of the present invention.

The compound of the present invention could be synthesized from the esterification of hydroxylphenyl benzofuran-2-one and benzoic acid derivatives. The following examples are exemplified to introduce the special aspects of the present invention, not to limit the scope of the present invention.

EXAMPLE 1

Synthesis of [4-tert-butyl-2-(5-tert-butyl-2-oxo-3H-benzofuran-3-yl)phenyl]benzoate (CT-500)

Mix 22.5 g heptane with 0.11 g Methanesulfonic acid, 11.25 g p-tert-butyl phenol and 5.65 g glyoxylic acid and reflux for dehydrate. Filter and dry the result solution to obtain 5-(tert-butyl)-3-[5-(tert-butyl)-2-hydroxyphenol]-benzofuran-2(3H)-one.

Figure 1:
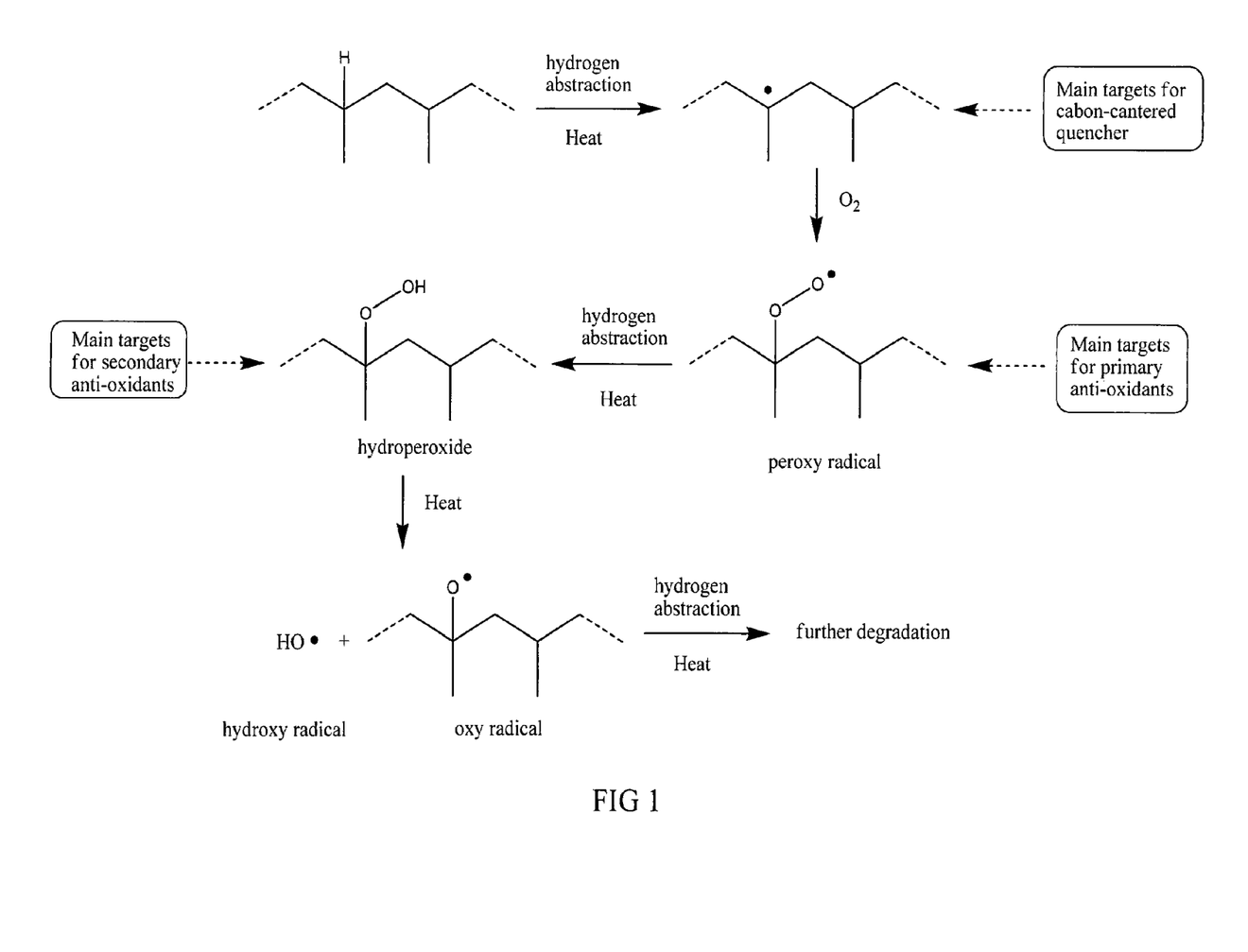
FIG. 1 is the schematic diagram of the mechanisms of various antioxidants.
Figure 2A:
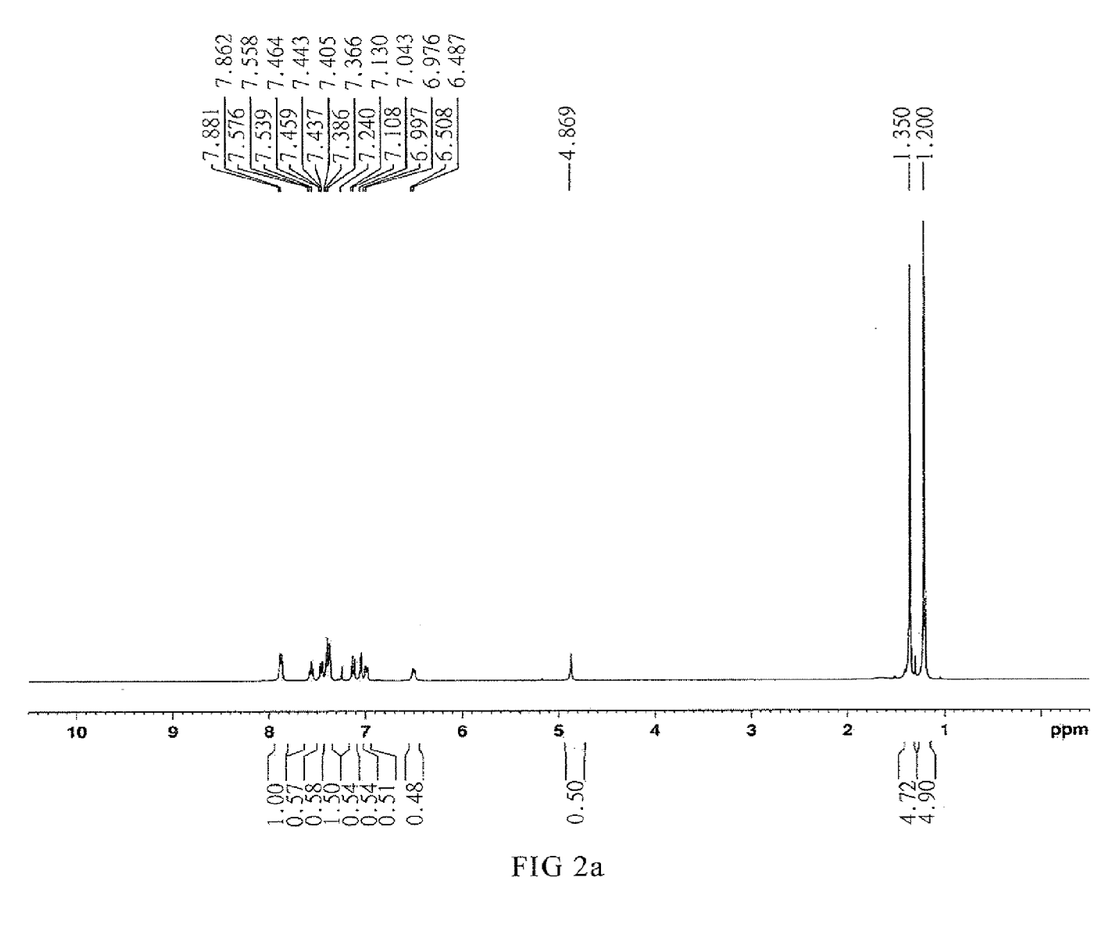
FIG. 2A is a NMR spectrometry of CT-500.
Figure 2B:
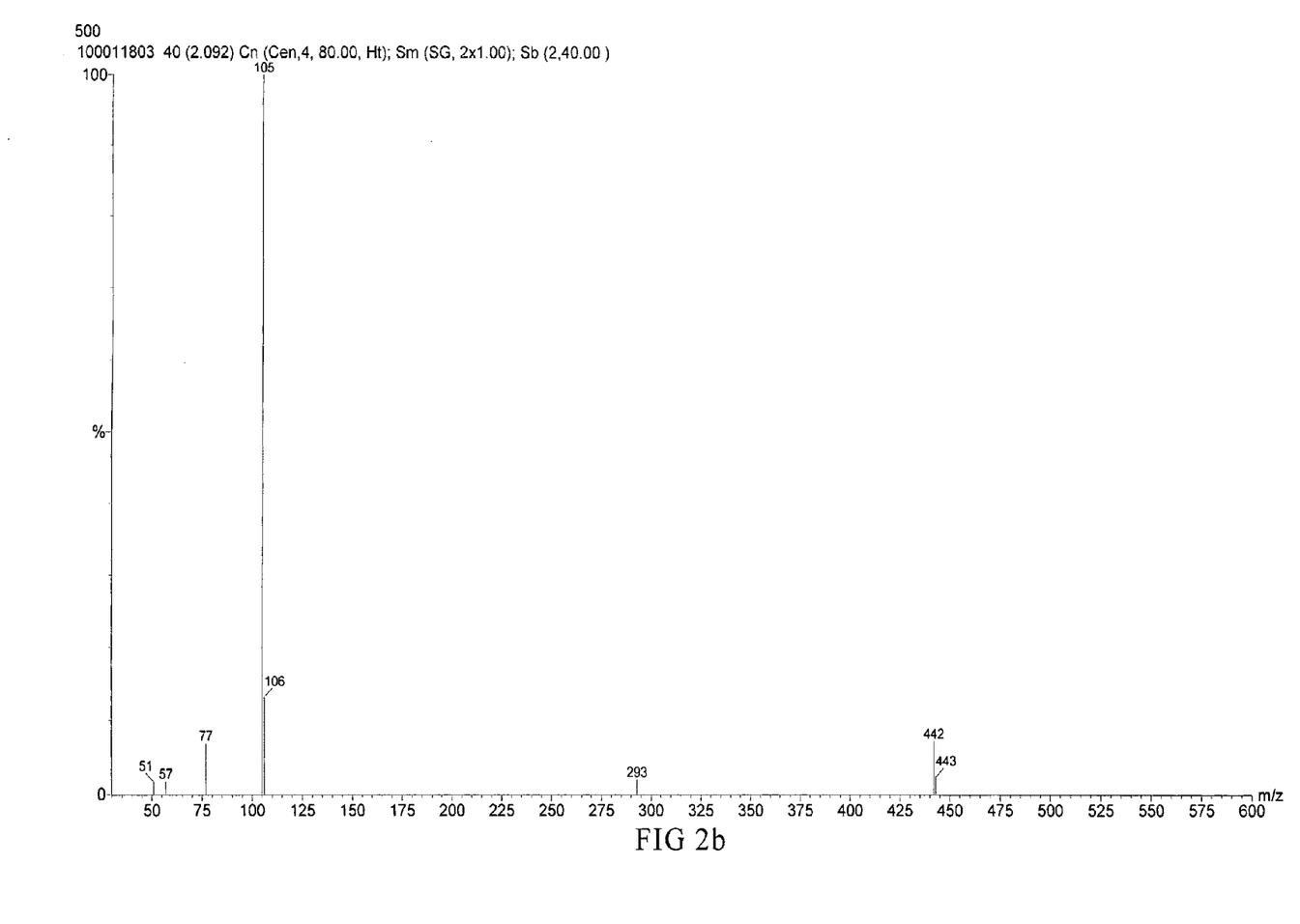
FIG. 2B is a mass spectrometry of CT-500.
Figure 2C:
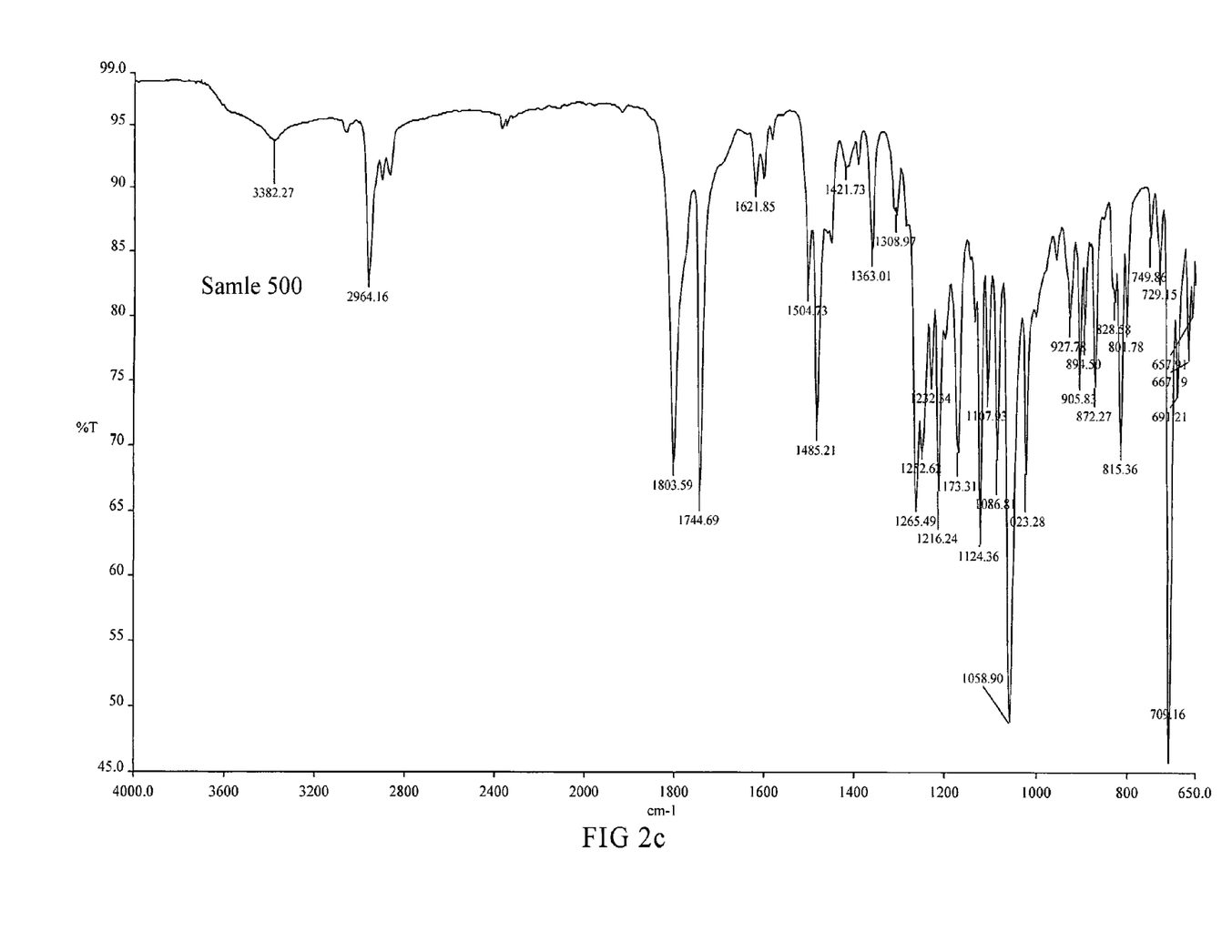
FIG. 2C is an IR spectrometry of CT-500.

Take 33.7 g (100 mmol) 5-(tert-butyl)-3-[5-(tert-butyl)-2-hydroxyphenol]-benzofuran-2(3H)-one, 12.81 g (105 mmol) benzoic acid and 70 mL toluene in a 250 mL three-necked round-bottom flask and add with 0.337 g (1.8 mol) p-toluenesulfonic acid. The mixture is refluxed to remove water by Dean-Stark apparatus for 6 hours. Cool down the mixture until the temperature goes down to 60° C. then add 5.4 g (35 mmol) phosphorus oxychloride and remove the Dean-Stark apparatus to reflux for 6 hours. The mixture is cooled down to room temperature (20° C.) and added 50 g water for neutralization. Separate the organic layer and extract solvent to get light yellow primary product. Mix the primary product with 100 g cyclohexane and heat to reflux for 1 hour to get the educt. Cool down the mixture solution to room temperature (20° C.) and filter it followed with drying by hot-air oven to get 37.6 g (85 mmol) white solid product with 95% yield and 99.6% purity. The identity information of the product are shown at FIGS. 2a-2b and 2c.

EXAMPLE 2

Synthesis of [4-tert-butyl-2-(5-tert-butyl-2-oxo-3H-benzofuran-3-yl)phenyl]-3,5-di(tert-butyl)-4-hydroxy-benzoate (CT-501)

Figure 3A:
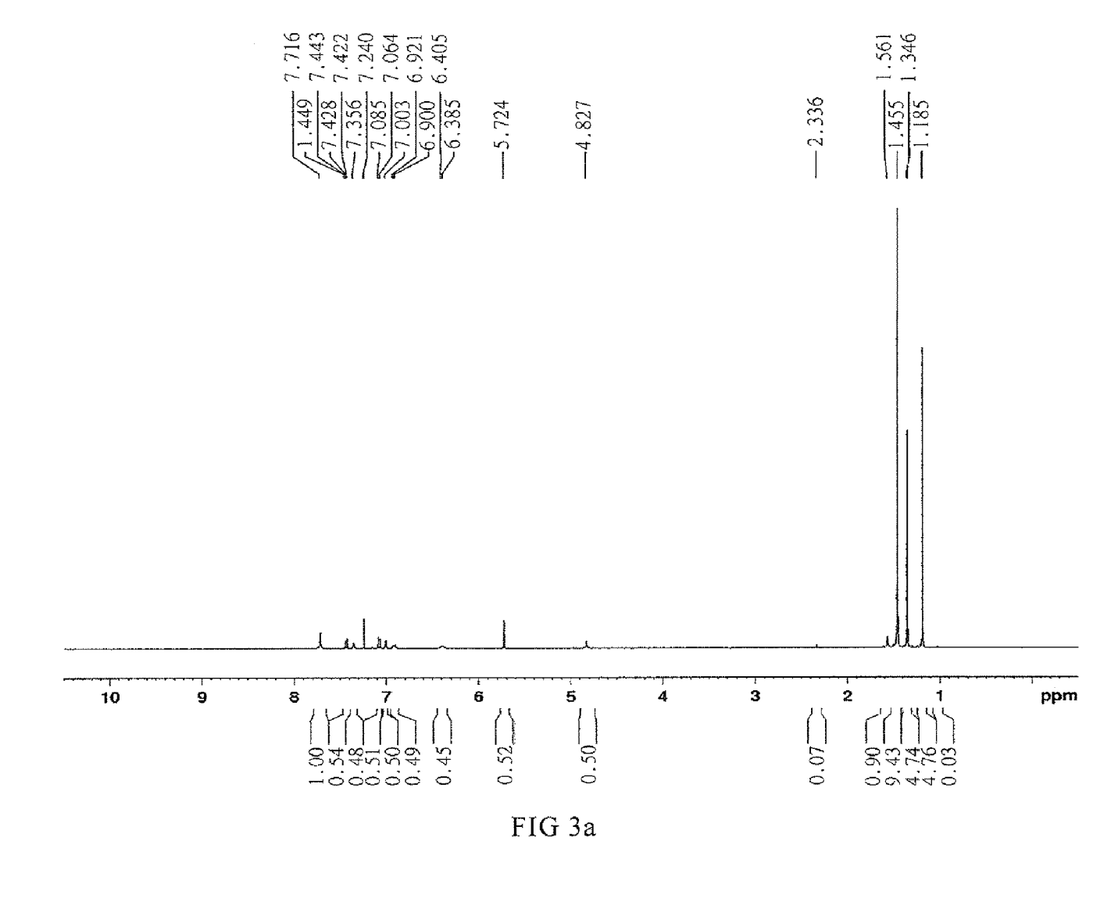
FIG. 3A is a NMR spectrometry of CT-501.
Figure 3B:
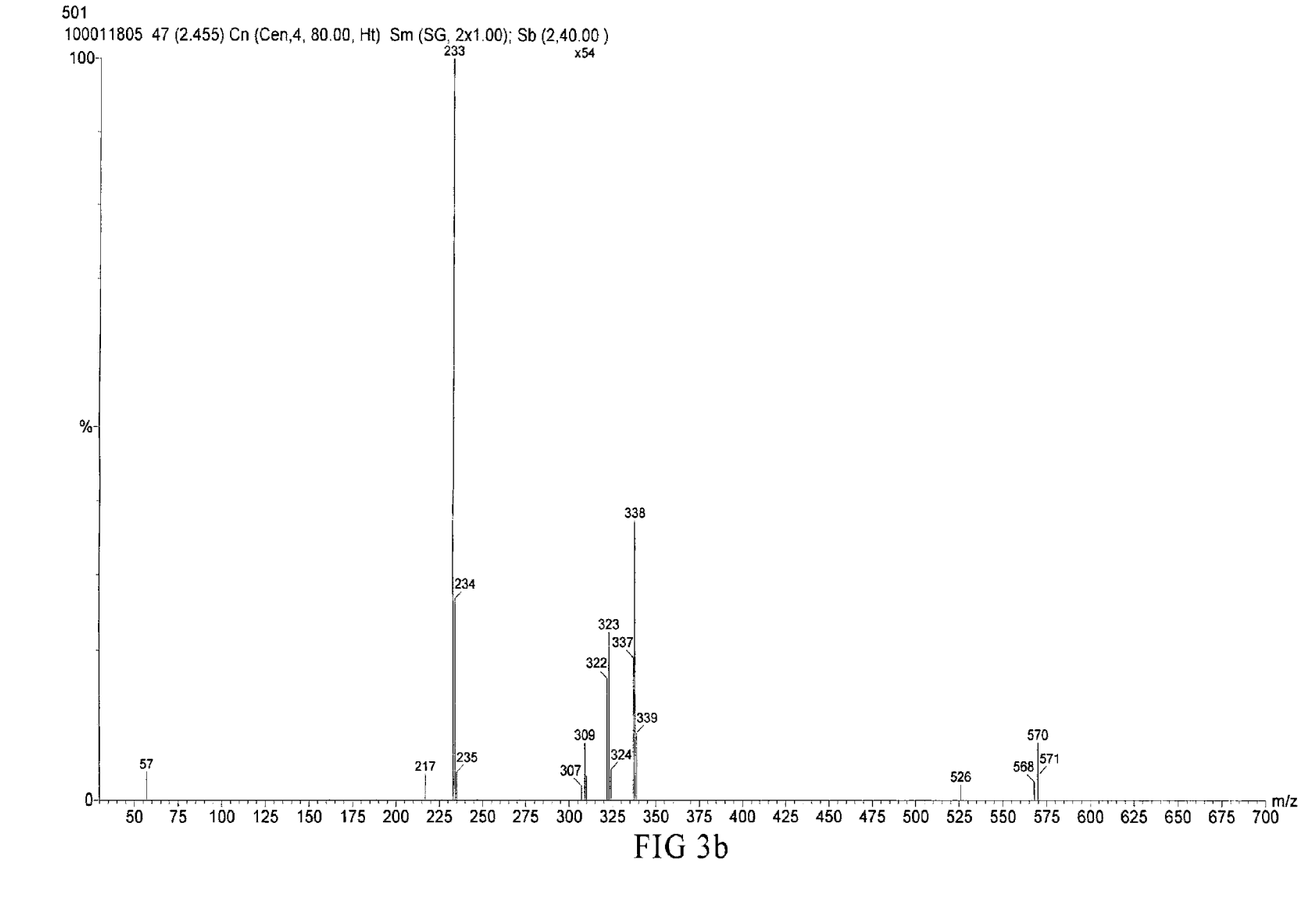
FIG. 3B is a mass spectrometry of CT-501.
Figure 3C:
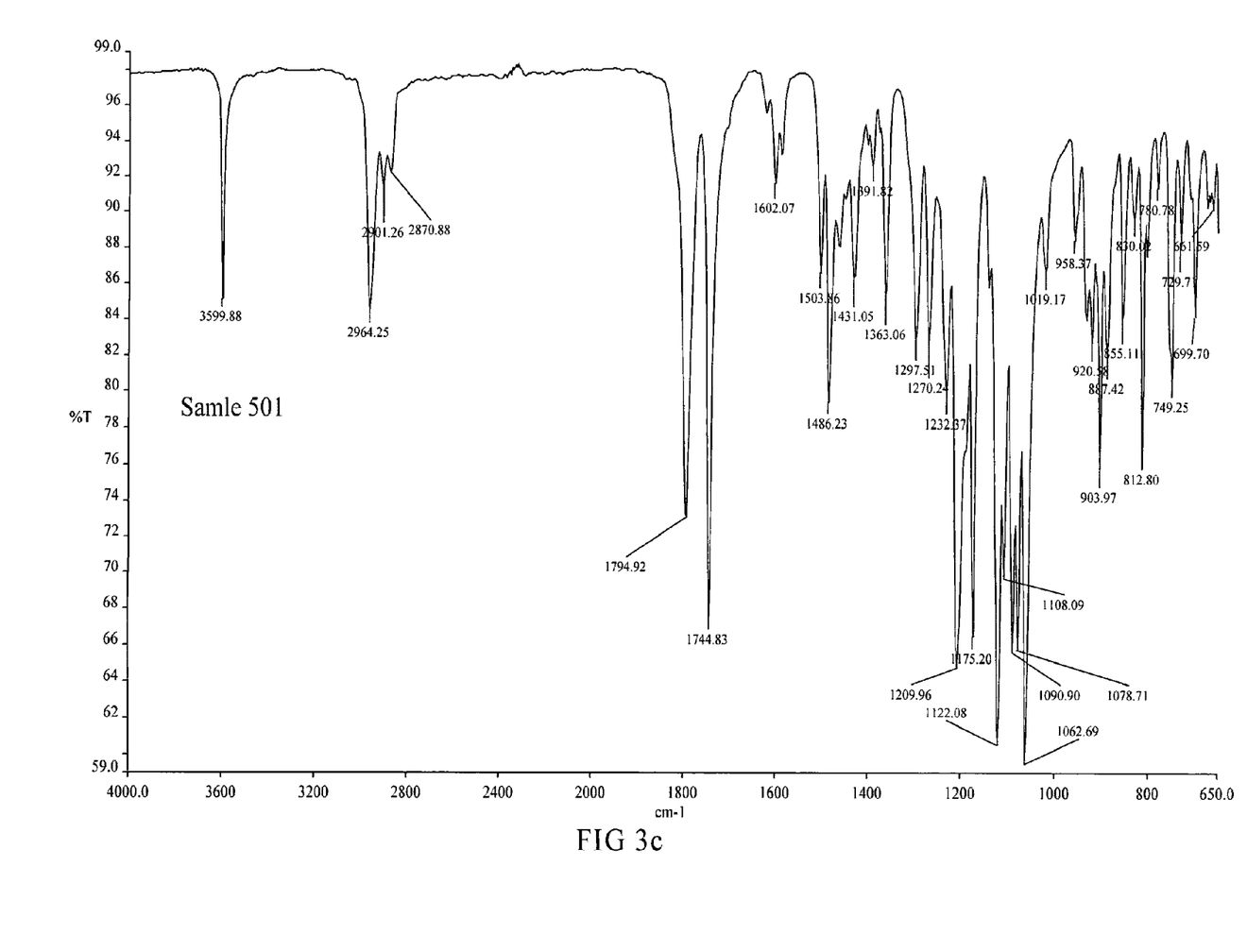
FIG. 3C is an IR spectrometry of CT-501.

Mix 22.5 g heptane with 0.11 g Methanesulfonic acid, 11.25 g p-tert-butyl phenol and 5.65 g glyoxylic acid and reflux for dehydrate. Filter and dry the result solution to obtain 5-(tert-butyl)-3-[5-(tert-butyl)-2-hydroxyphenol]-benzofuran-2(3H)-one. Take 33.7 g (100 mmol) 5-(tert-butyl)-3-[5-(tert-butyl)-2-hydroxyphenol]-benzofuran-2(3H)-one, 26.3 g (105 mmol) 3,5-di(tert-butyl)-4-hydroxy-benzoic acid and 70 mL toluene in a 250 mL three-necked round-bottom flask and add with 0.337 g (1.8 mmol) p-toluenesulfonic acid. The mixture is refluxed to remove water by Dean-Stark apparatus for 6 hours. Cool down the mixture until the temperature down to 60° C. then add 5.4 g (35 mmol) phosphorus oxychloride and remove the Dean-Stark apparatus to reflux for 6 hours. The mixture is cooled down to room temperature (20° C.) and added 50 g water for neutralization. Separate the organic layer and extract solvent to get light yellow primary product. Mix the primary product with 100 g methanol and heat to reflux for 1 hour to get the educt. Cool down the mixture solution to room temperature (20° C.) and filter it followed with drying by hot-air oven to get 45.6 g (80 mmol) white solid product with 80% yield and 99.8% purity. The identity information of the product are shown at FIGS. 3a-3b and 3c.

EXAMPLE 3

Synthesis of [4-tert-butyl-2-(5-tert-butyl-2-oxo-3H-benzofuran-3-yl)phenyl]-3-[3,5-di(tert-butyl)-4-hydroxyphenol]-propanoate (CT-502)

Mix 22.5 g heptane with 0.11 g Methanesulfonic acid, 11.25 g p-tert-butyl phenol and 5.65 g glyoxylic acid and reflux for dehydrate. Filter and dry the result solution to obtain 5-(tert-butyl)-3-[5-(tert-butyl)-2-hydroxyphenol]-benzofuran-2(3H)-one. Take 33.7 g (100 mmol) 5-(tert-butyl)-3-[5-(tert-butyl)-2-hydroxyphenol]-benzofuran-2(3H)-one, 29.23 g (105 mmol) 3-[3,5-di(tert-butyl)-4-hydroxyphenyl]propanic acid, 0.337 g (1.8 mol) p-toluenesulfonic and 70 mL dichloromethane in a 250 mL three-necked round-bottom flask and add with 17.84 g (150 mmol) thionyl chloride. The mixture is stirred in ice bath (5° C.) for 3 days. Warm the mixture until the temperature up to room temperature (20°

Figure 4A:
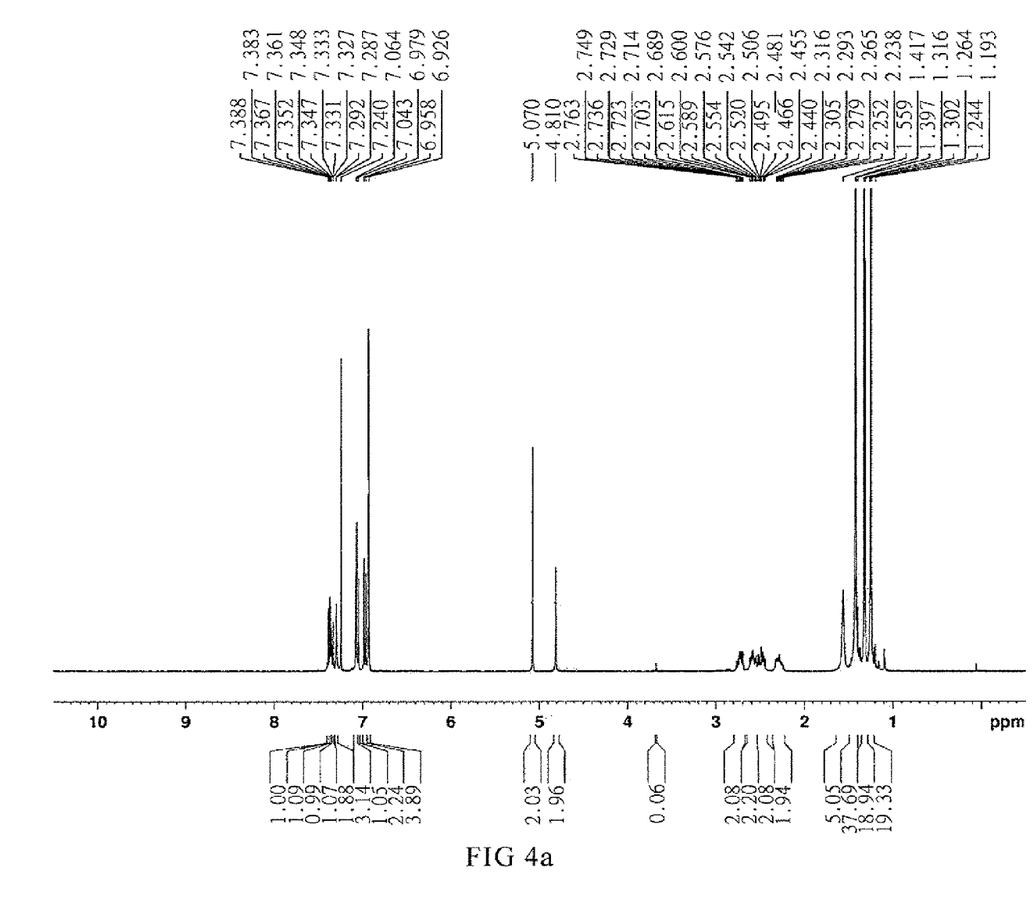
FIG. 4A is a NMR spectrometry of CT-502.
Figure 4B:
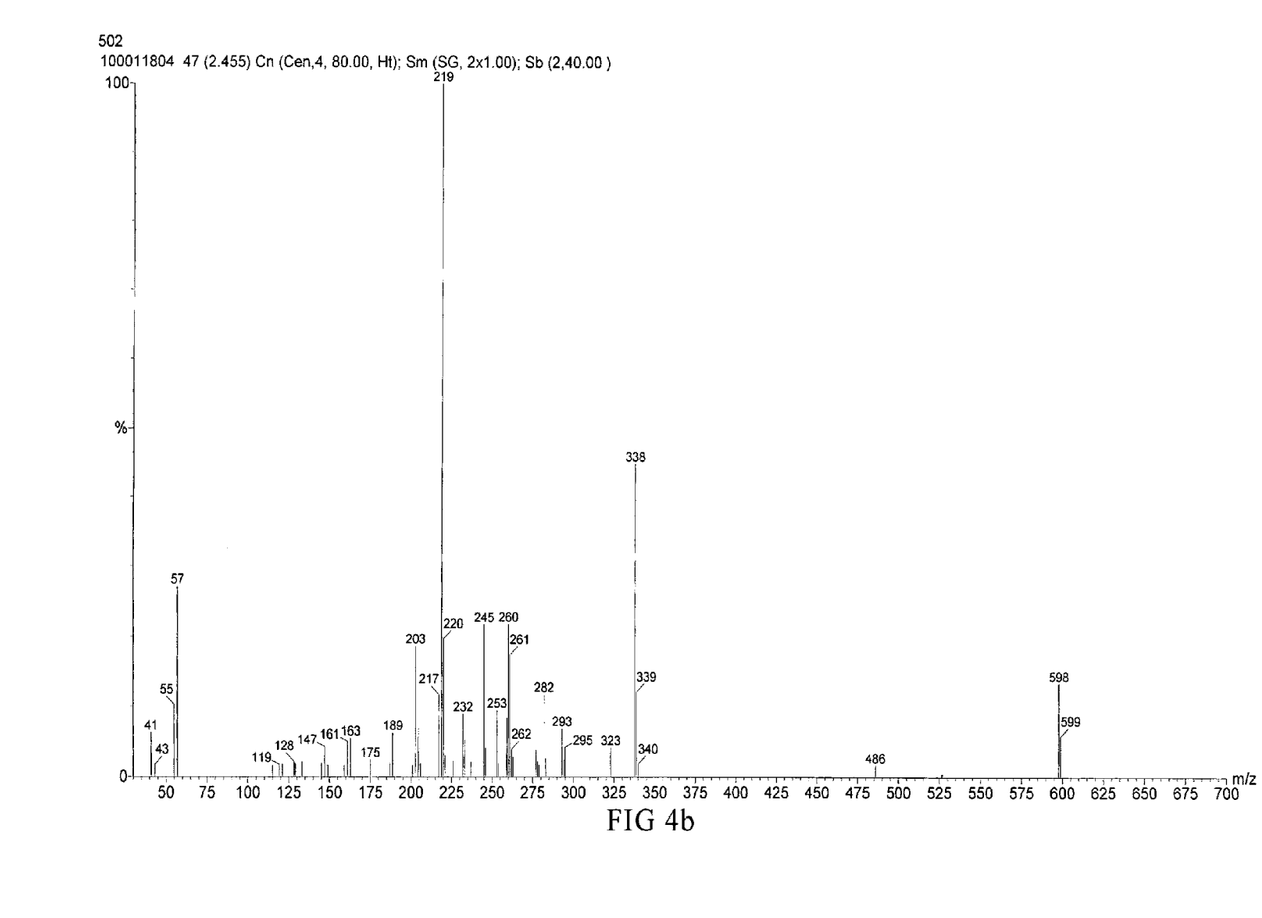
FIG. 4B is a mass spectrometry of CT-502.
Figure 4C:
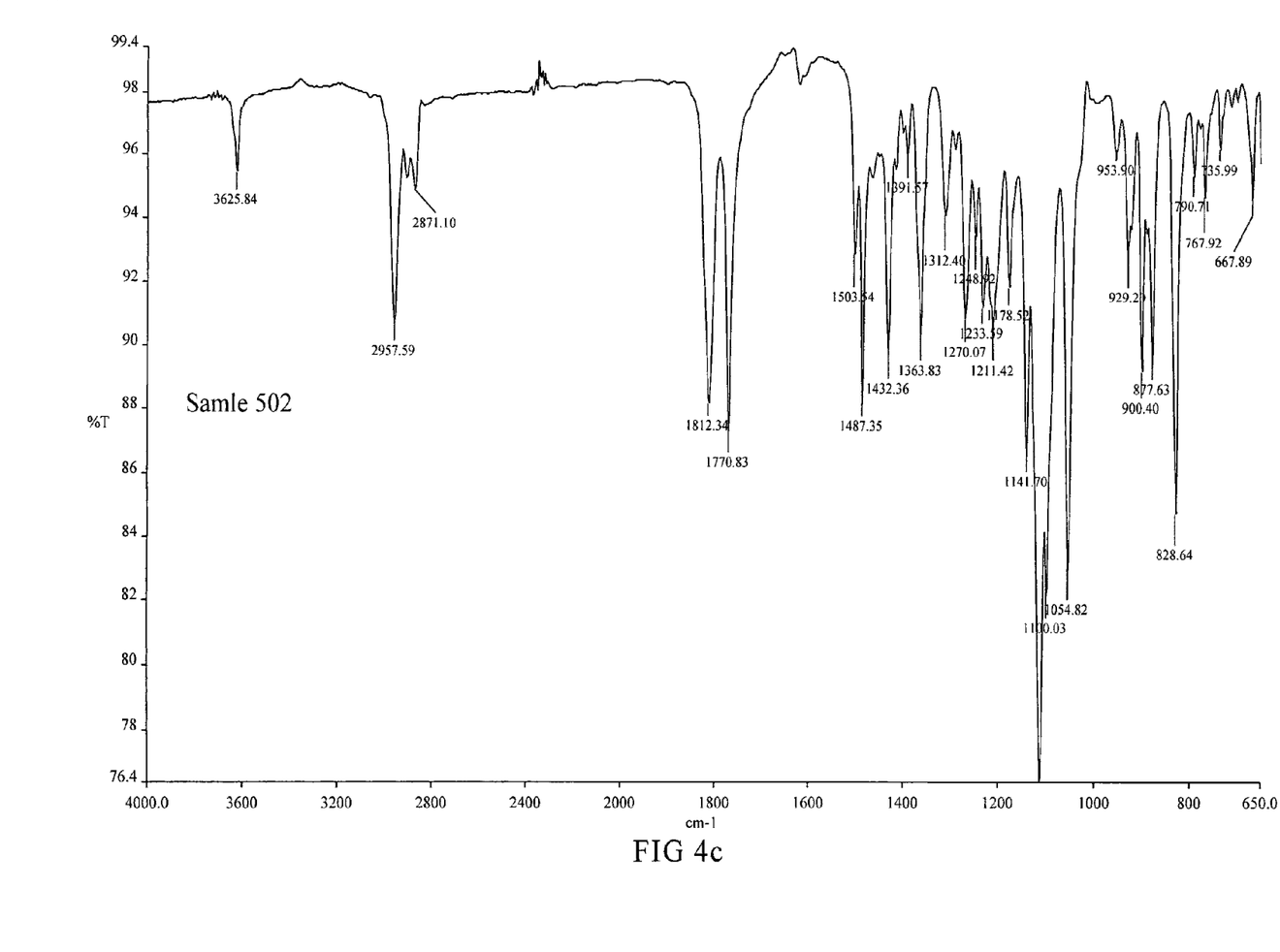
FIG. 4C is an IR spectrometry of CT-502.

C.) and added 50 g water for neutralization. Separate the organic layer and extract solvent to get light yellow primary product. Mix the primary product with 100 g cyclohexane and heat to reflux for 1 hour to get the educt. Filter the result solution and dry by hot-air oven to get 35.96 g (63 mmol) white solid product with 63% yield and 99.8% purity. The identity information of the product are shown at FIGS. 4a-4b and 4c.

EXAMPLE 4

The Applied Characteristic Analysis of the Compounds of the Present Invention

To prove the stability of the compounds of the present invention, we design a formulation which the present invention is added into the commercialized antioxidant. The melt flow rate (MFR) and color stability (Yi) of these formulations are tested. The hydrotalcite is used as a hydrolysis stabilizer.

| | Experiment | | | |
|---|---|---|---|---|
| Contents in the formula | formula 1 (without the compound of the present invention) | formula 2 (Benzoic acid) | formula 3 (carbon-centered radical quencher antioxidant and primary antioxidant) | formula 4 carbon-centered radical quencher antioxidant and primary antioxidant |
| Deox 604 | 1.62 g | 1.62 g | 1.62 g | 1.62 g |
| Deox 10 | 0.675 g | 0.675 g | 0.675 g | 0.675 g |
| Example 1 CT-500 | | 0.135 g | | |
| Example 2 CT-501 | | | 0.135 g | |
| Example 3 CT-502 | | | | 0.135 g |
| hydrotalcite | 0.27 g | 0.27 g | 0.27 g | 0.27 g |

Wherein, Deox 604 and Deox 10 are commodities purchased from Chitec Chemical Co., LTD.

Melt Flow Rate (MFR) Testing

The MFR is obtained from polypropylene added with 0.06% by weight of the aforesaid formulations and 0.1% by weight of calcium stearate. The ratio is listed in the following table:

| | Group | | | |
|---|---|---|---|---|
| ratio | No. 1 (control) | No. 2 | No. 3 | No. 4 |
| Polypropylene (pp) | 99.84% | 99.84% | 99.84% | 99.84% |
| formula 1 | 0.06% | | | |
| formula 2 | | 0.06% | | |
| formula 3 | | | 0.06% | |
| formula 4 | | | | 0.06% |
| calcium stearate | 0.1% | 0.1% | 0.1% | 0.1% |

Figure 5:
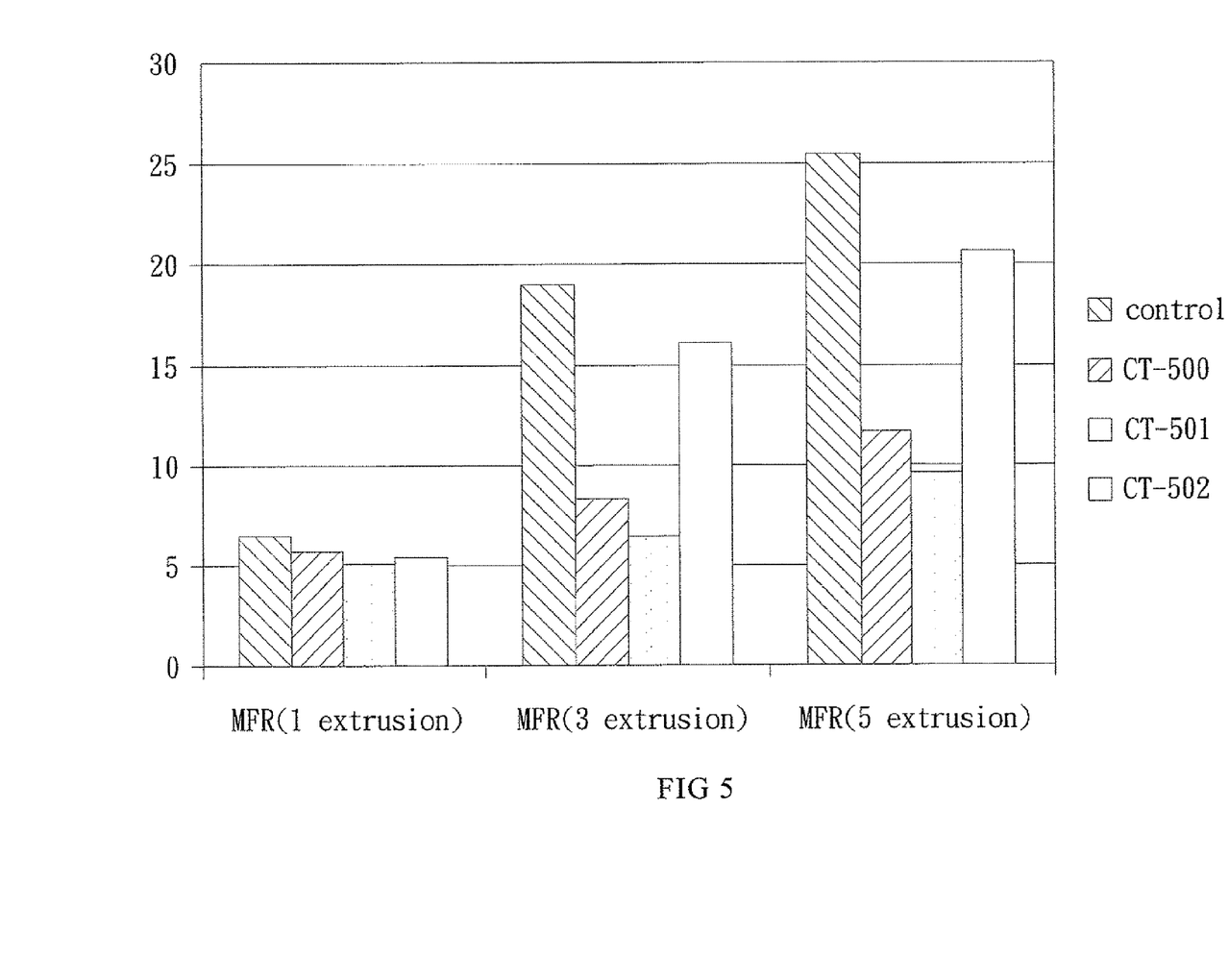
FIG. 5 is the measured result of melt flow rate of the polymer added with the antioxidant of the present invention and the control polymer without the adding of antioxidant.

The polypropylenes are extruded once, three times and five times respectively by twin-screw extruder (Coperion STS 35, L/D=36) under the conditions of 220° C. and 40-50 rpm, followed by sampling for the MFR test. The test is based on ASTM D1238 and proceeded under the conditions of 190° C. and 2.16 kg, and the unit of the obtained data is g/10 min. The data had been collected to plot FIG. 5. The Y axis coordinate is the value of MFR, and the X axis coordinate represents the assigned numbers of the control and the experiment formulations extruded once, three times and five times. FIG. 5 indicates that groups 2, 3 and 4 added with the compound of the present invention have a smaller variation of MFR than group 1. It shows that the compound of the present invention is contributive for maintaining the characteristics of polymer.

Color Difference Test

Figure 6:
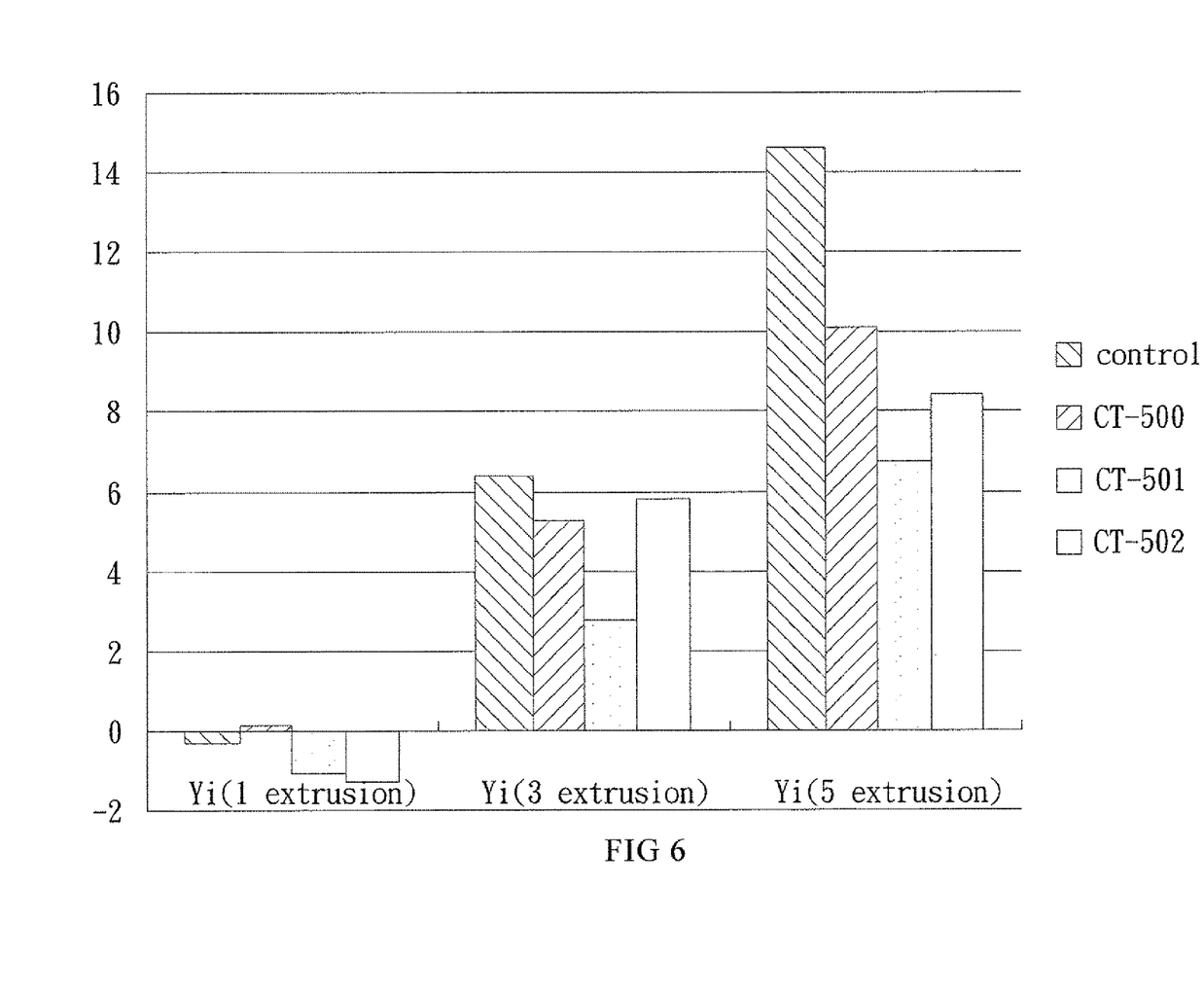
FIG. 6 is the measured result of the color stability test of the polymer added with the antioxidant of the present invention and the control polymer without the adding of antioxidant.

The test relates to how compound of the present invention influences the color stability of polymer, and it is processed by the aforesaid polypropylene formulations with once, three times and five times extrusion. The values obtained from the colorimeter (Nippon Denshoku, ZE2000) are collected to plot the FIG. 6. The Y axis coordinate is the value of color difference (Yi), and the X axis coordinate represents the assigned numbers of the control and the experiment formulations extruded once, three times and five times. FIG. 6 indicates that groups 2, 3 and 4 added with the compound of the present invention have a smaller variation of Yi than group 1. It shows that the compound of the present invention is contributive for maintaining the characteristics of polymer, especially for improving the antioxidization ability and processing resistance of polymer materials.

In conclusion, the benzofuranone derivatives of the present invention are provided with a greater molecular weight, and the proportion of the carbon-centered radical antioxidant is lower under the same weight condition. Nevertheless, the benzofuranone derivatives provide a synergistic antioxidation capability because a primary antioxidant portion is contained. We surprisingly discover that the compound provided by Example 2 has excellent performances in MFR test and color difference test, which proves that the compounds of the present invention could be used as a thermal stability protector for plastics, thus it is a new antioxidant component.

The embodiments and the technical principles used are described above. All variations and modifications of the present invention and the uses thereof are included in the scope of the present invention if they do not depart from the spirit of the disclosure of this specification.

What we claim are:

1. A benzofuranone derivative with antioxidant ability, wherein said derivative is a compound of formula (II), (III) or (IV) as follows:

2. The derivative of claim 1, wherein said compound is a compound of formula (II).

3. The derivative of claim 1, wherein said compound is a compound of formula (III).

4. The derivative of claim 1, wherein said compound is a compound of formula (IV).

5. A method for stabilizing organic materials, wherein said method comprises adding a compound of the following formula (II), (III) or (IV) onto said organic materials:

6. The method of claim 5, wherein said compound is used as an antioxidant.

7. The method of claim 5, wherein the quantity of said compound relative to said organic materials is 0.01%~10% by weight.

8. The method of claim 7, wherein the quantity of said compound relative to said organic materials is 0.1%~2% by weight.

9. The method of claim 5, wherein said organic materials are polymer materials.

10. The method of claim 5, wherein said compound is a compound of formula (II).

11. The method of claim 5, wherein said compound is a compound of formula (III).

12. The method of claim 5, wherein said compound is a compound of formula (IV).

* * * * *